United States Patent [19]

Rotgans

[11] 4,085,741
[45] Apr. 25, 1978

[54] APPARATUS FOR EFFECTING PLETHYSMOGRAPHY

[75] Inventor: Gerrit Jacob Rotgans, Hilversum, Netherlands

[73] Assignee: Gould Godart B.V., Bilthoven, Netherlands

[21] Appl. No.: 713,606

[22] Filed: Aug. 11, 1976

[51] Int. Cl.² .............................................. A61B 5/08
[52] U.S. Cl. .................................................. 128/2.08
[58] Field of Search ................ 128/2.08, 2.05 V, 2 R, 128/DIG. 29

[56] References Cited

U.S. PATENT DOCUMENTS

| 2,569,849 | 10/1951 | Emerson | 128/2.08 |
| 3,511,237 | 5/1970 | Jaeger | 128/2.08 |

FOREIGN PATENT DOCUMENTS

| 1,516,419 | 8/1969 | Germany | 128/2.08 |
| 2,415,537 | 10/1975 | Germany | 128/2.08 |

OTHER PUBLICATIONS

Bartlett, R. G. et al, *Journ. of Applied Physiology*, vol. 14, (1959), pp. 89–96.
Jaeger, M. J. et al., Journ. of Applied Physiology, vol. 19, Jul. (1964), pp. 813–820.

*Primary Examiner*—Kyle L. Howell
*Attorney, Agent, or Firm*—Haseltine, Lake & Waters

[57] ABSTRACT

Plethysmograph apparatus comprising a measuring cell and a reference cell constructed in such manner that exterior pressure variations cause equal pressure variations in both cells. The measuring cell is transparent. The quantity to be measured is the pressure difference between the two cells. A mechanism is provided for adjusting the ratio of the volume to the compliance of the reference cell, so that this ratio may be made exactly equal to the corresponding ratio for the measuring cell. The adjustment may be performed by adjusting the force exerted on a membrane, which has been inserted in a wall of the reference cell.

4 Claims, 2 Drawing Figures

APPARATUS FOR EFFECTING PLETHYSMOGRAPHY

BACKGROUND OF THE INVENTION (a) Field of the Invention

The invention relates to an apparatus for effecting plethysmography, comprising a measuring cell adapted to enclose a person to be examined, and mainly consisting of a transparent material, a smaller reference cell constructed in such manner that exterior pressure variations cause equal pressure variations within both cells, and means for measuring the difference between the pressure in the two cells.

(b) Prior Art

Plethysmography is a method for measuring the volume variations of the thorax of a person to be examined during respiration. For this purose the person is enclosed in an airtight measuring cell, so that the volume variations of the thorax cause pressure variations within the measuring cell. These pressure variations may be measured, and may be used to determine the volume variations of the thorax with the aid of suitable tables. Of course, the pressure variations occurring in the measuring cell are extremely small, so that the measurement is strongly disturbed by pressure variations in the atmosphere outside the measuring cell, for instance due to the opening and closing of doors, vibrations, sounds, and the like.

It is known to reduce the influence of the exterior pressure variations by using a reference cell of smaller dimensions, which is constructed in such manner that the exterior pressure variations cause equal pressure variations in both cells, and by measuring the pressure difference between the two cells. In order to obtain an exact compensation of the exterior pressure variations, the reference cell must satisfy the condition that the ratio of the volume to the compliance must be equal to the corresponding ratio for the measuring cell. In this connection, the compliance of a cell may be defined as a positive value corresponding to the derivative of the volume as a function of the difference between the pressure outside and inside the cell.

It is usual to make the measuring cell as rigid as possible, so that the influence of the exterior pressure variations is reduced to a minimum. To satisfy this requirement, the measuring cell is generally made of an opaque material, and only provided with a small window in the wall to observe the patient. However, the person to be examined feels very uncomfortable in a cell of this kind, since he is locked up in a small space, and completely isolated from the surroundings. It has been proposed to remove this disadvantage by the use of a transparent synthetic material, such as polymethylmethacrylate, for the walls of the measuring cell, but expensive and complicated constructions have been necessary in this case to obtain a sufficient rigidity of the measuring cell, since the natural rigidity of the material is very small.

An apparatus for effecting plethysmography comprising an opaque measuring cell with a small window in the wall has been disclosed in Dutch Patent application No. 65,16124, laid open to public inspection on June 13, 1966.

An apparatus for effecting plethysmography comprising a measuring cell made of a transparent material whose rigidity has been increased by a special construction has been disclosed in an article by F. D. Stott, entitled "The Whole-body Plethysmograph", and published in the British periodical "Instrument Practice", Jan. 1963, pages 48–51.

Both above-mentioned publications also disclose a reference cell for compensating exterior pressure variations.

SUMMARY OF THE INVENTION

It is an object of the invention to improve the known constructions and to make it possible to use a transparent measuring cell without the necessity of an expensive and complicated construction.

It is a further object of the invention to provide effective means for adjusting the compliance of a reference cell used in plethysmography.

According to the invention, means are provided for adjusting the ratio of the volume to the compliance of the reference cell, so that this ratio may be made exactly equal to the corresponding ratio for the measuring cell.

The invention is based on the recognition that an extremely rigid construction of the measuring cell is not necessary, provided that the compensation of the exterior pressure variations is carried out with sufficient accuracy.

The said ratio may be adjusted by adjusting either the volume, or the compliance of the reference cell, or by adjusting both the said values. It is preferred, however, to render the compliance adjustable.

The adjustability of the compliance of the reference cell may be obtained by inserting a membrane in a wall of the reference cell, and by exerting an adjustable force on said membrane. In a preferred embodiment of the invention, the membrane is loaded by a spring having a non-linear characteristic, and the force exerted on the membrane by said spring is rendered adjustable by means of a screw.

DETAILED DESCRIPTION

Figure 1:
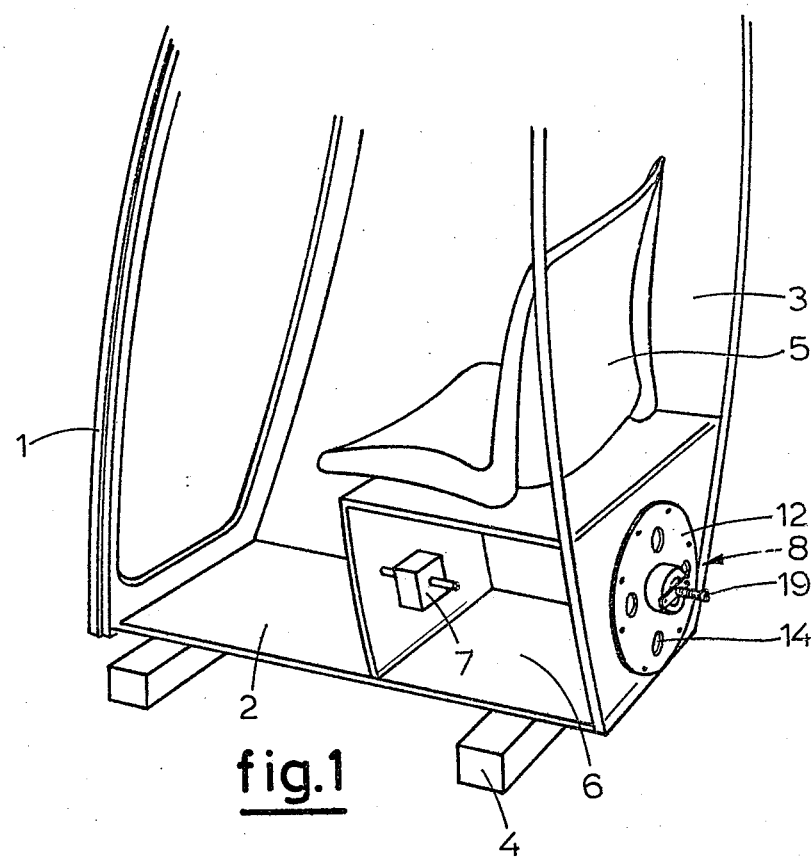
FIG. 1 shows schematically a measuring cell, and a reference cell having an adjustable compliance, which is arranged underneath a seal for the patient.

The apparatus shown in FIG. 1 comprises a measuring cell 1, consisting of a frame, carrying a floor 2, four upstanding walls 3 made of a transparent synthetic material, and a top wall (not shown). The measuring cell is supported by two beams 4. No special measures have been taken to increase the rigidity of the measuring cell.

The measuring cell 1 contains a seat 5 for the patient. The front wall of the cell is constructed as a door which is pivotable about its upper edge, and through which the patient may enter the cell.

A reference cell 6 is arranged underneath the seat 5. However, the seat 5 is separately supported, so that the reference cell is not loaded by the weight of the patient. A differential pressure meter 7 is arranged in or near the partition between the measuring cell and the reference cell. This pressure meter communicates with the measuring cell on one side, and with the reference cell on the other side, and measures the pressure difference between the two cells. The volume variations of the thorax of the patient may be derived from this pressure difference with the aid of the above-mentioned tables.

The differential pressure meter 7 may be of any conventional construction. For instance, the pressure meter may contain a diaphragm adapted to be displaced by any pressure difference between the two cells, and two electrodes arranged on both sides of the diaphragm and forming condensers with the same. A displacement of the diaphragm causes a change of the capacity ratio between the two condensers, which may be observed by electric means.

The back wall of the reference cell 6 contains a device 8 for adjusting the compliance of the reference cell. The device 8 has been separately shown in FIG. 2.

Figure 2:
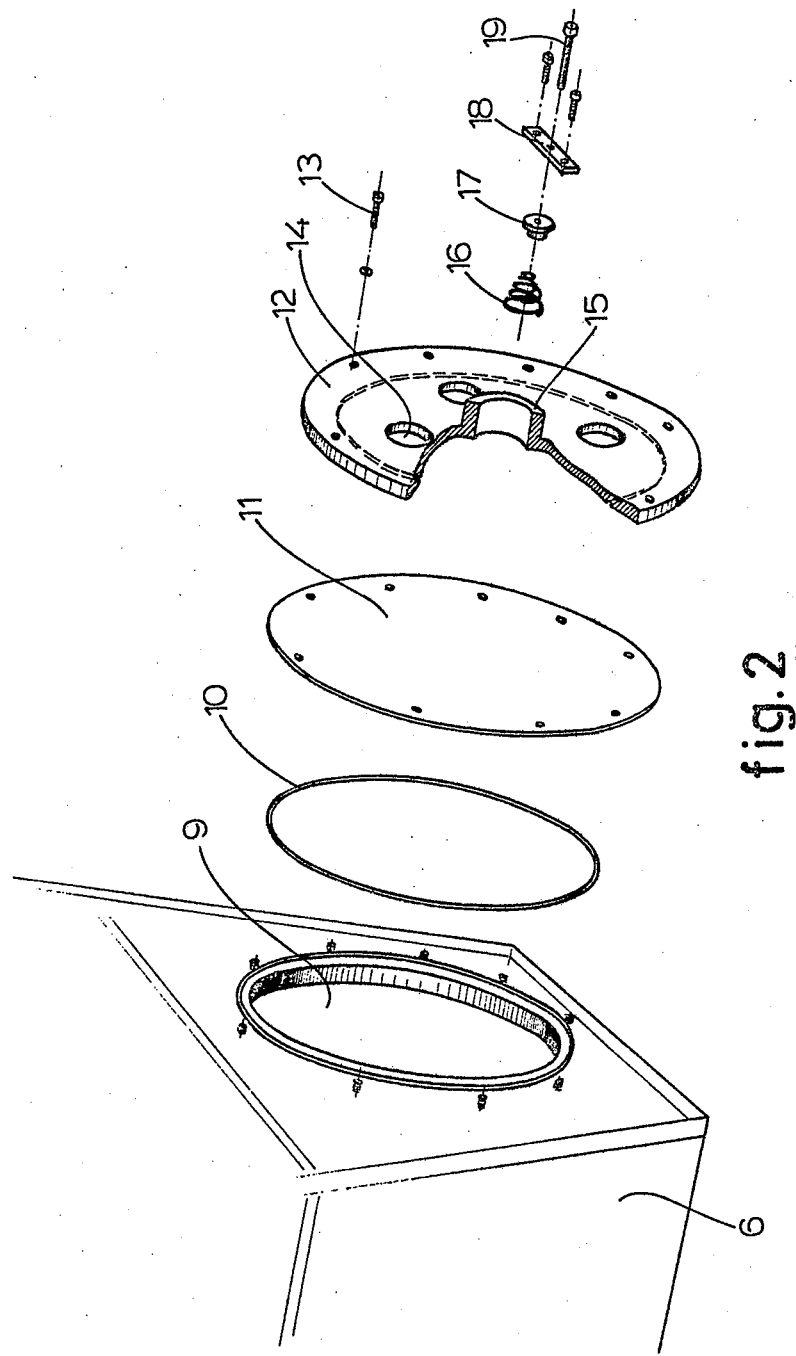
FIG. 2 shows an exploded view of means for adjusting the compliance of the reference cell.

According to FIG. 2, the back wall of the reference cell 6 is provided with an opening 9 for receiving the adjusting device. A gasketing ring 10 is arranged against the edge of the opening 9. A thin membrane 11 is placed against the ring 10, and the assembly is retained by means of a closure plate 12, secured to the back wall of the reference cell 6 by means of screws 13. The closure plate 12 is provided with a plurality of holes 14, so that the membrane 11 is exposed to the atmospheric pressure.

Furthermore, the closure plate 12 comprises a hub 15, enclosing a compression spring 16 having a non-linear characteristic, and lying against the membrane 11. A pressure member 17, retained by a plate 18 screwed onto the plate 18, exerts a force on the spring 16. The pressure member 17 may be displaced by means of an adjusting screw 19, arranged in an internally threaded bore of the plate 18. Thus, the force exerted on the membrane 11 by the spring 16 may be controlled by means of the screw 19.

The rigidity of the membrane 11 is dependent on the force exerted thereon, so that the compliance of the reference cell may be adjusted by means of the screw 19.

In principle, it is also possible to adjust the volume of the reference cell instead of the compliance; however, such an adjustment is more difficult to realize.

By means of the adjusting device 8, the compliance of the reference cell may be adjusted with such accuracy that the limited rigidity of the measuring cell does not lead to any difficulties.

The invention is not restricted to the above-described embodiment, which may be modified in various ways within the scope of the appended claims. I claim:

1. Apparatus for effecting plethysmography, comprising an airtight measuring cell adapted to enclose a person to be examined, and constituted substantially of a compliant transparent material such that the compliance of said measuring cell is substantially determined by the rigidity of said material, a smaller reference cell having a measurable volume and compliance, said reference cell being disposed within said measuring cell such that exterior pressure variations cause equal pressure variations in both cells, means for measuring the difference between the pressures in said two cells, and means for adjusting the ratio of the volume to the compliance of said reference cell, so that this ratio may be made exactly equal to the corresponding ratio for said measuring cell.

2. Apparatus as claimed in claim 1, wherein said ratio is adjusted by adjusting the compliance of said reference cell.

3. Apparatus as claimed in claim 2, further comprising a membrane inserted in a wall of said reference cell, said adjusting means comprising means for exerting a force on said membrane, and means for adjusting said force.

4. Apparatus as claimed in claim 3, wherein the said force exerting means comprises a spring bearing against said membrane and having a non-linear characteristic, and a screw for adjusting the force exerted by said spring on said membrane.

* * * * *